United States Patent
Nukui et al.

(10) Patent No.: US 7,088,800 B2
(45) Date of Patent: Aug. 8, 2006

(54) X-RAY CT SYSTEM AND BEAM-HARDENING POST-PROCESSING METHOD

(75) Inventors: Masatake Nukui, Tokyo (JP); Shunichiro Tanigawa, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 187 days.

(21) Appl. No.: 10/825,526

(22) Filed: Apr. 15, 2004

(65) Prior Publication Data

US 2004/0208290 A1    Oct. 21, 2004

(30) Foreign Application Priority Data

Apr. 17, 2003  (JP) .............................. 2003-112906

(51) Int. Cl.
*A61B 6/03* (2006.01)
(52) U.S. Cl. ...................................................... 378/18
(58) Field of Classification Search ................. 378/18, 378/207
See application file for complete search history.

(56) References Cited

U.S. PATENT DOCUMENTS

| | | | |
|---|---|---|---|
| 4,352,020 A * | 9/1982 | Horiba et al. ................. 378/18 |
| 4,870,666 A | 9/1989 | Lonn et al. | |
| 5,565,678 A * | 10/1996 | Manian ....................... 378/207 |
| 5,774,519 A | 6/1998 | Lindstrom et al. | |
| 5,867,553 A | 2/1999 | Gordon et al. | |
| 5,953,444 A | 9/1999 | Joseph et al. | |
| 6,430,252 B1 | 8/2002 | Reinwand et al. | |
| 6,438,197 B1 | 8/2002 | Stierstorfer | |
| 6,505,966 B1 | 1/2003 | Guru | |
| 6,507,633 B1 | 1/2003 | Elbakri et al. | |
| 6,944,258 B1 * | 9/2005 | Nukui et al. .................... 378/4 |
| 2004/0196960 A1 * | 10/2004 | Tanigawa et al. ........... 378/207 |

FOREIGN PATENT DOCUMENTS

JP          05-130987         5/1993

\* cited by examiner

*Primary Examiner*—Edward J. Glick
*Assistant Examiner*—Chih-Cheng Glen Kao
(74) *Attorney, Agent, or Firm*—Carl B. Horton, Esq.; Armstrong Teasdale LLP

(57) ABSTRACT

An X-ray computed tomographic (CT) system includes: a beam-hardening correction block that corrects first projection information in terms of the beam-hardening effect so as to produce second projection information; a first fitting block that fits a first function to the second projection information so as to produce third projection information; a second fitting block that fits a second function to the third projection information values that are provided as functions having as independent variables the second projection information values sampled in relation to all the views and each of the channels of an X-ray detector; and a correction coefficient modification block that modifies a second correction coefficient, which is calculated using a second phantom larger in dimensions than a first phantom, using a first correction coefficient calculated using the first phantom.

16 Claims, 13 Drawing Sheets

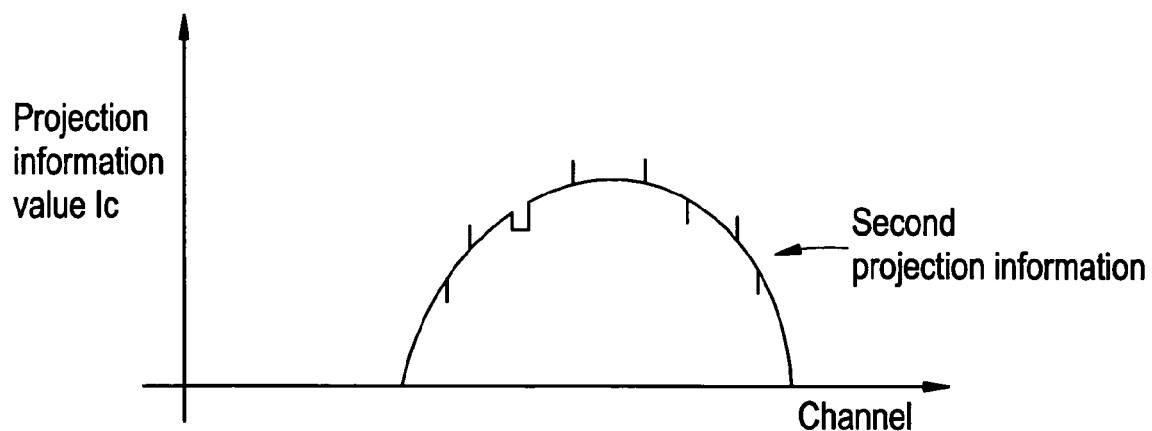
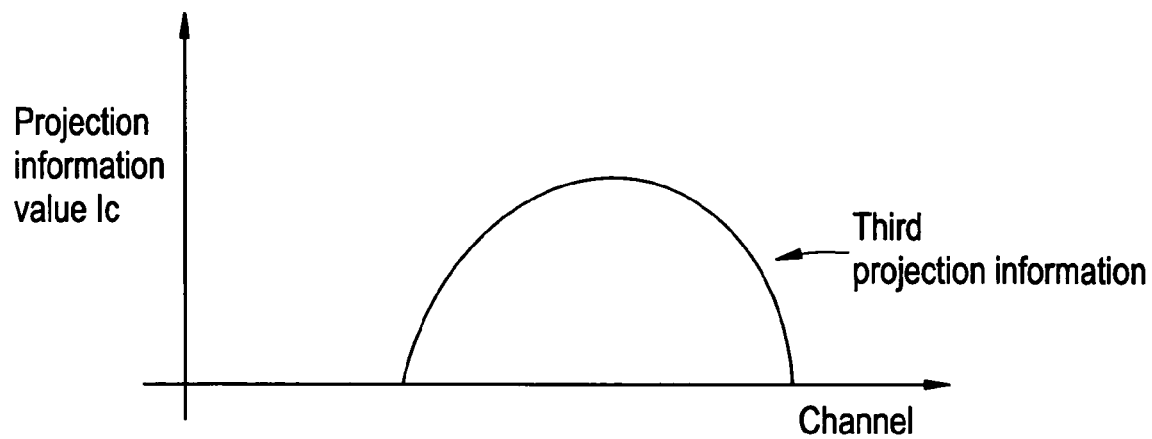

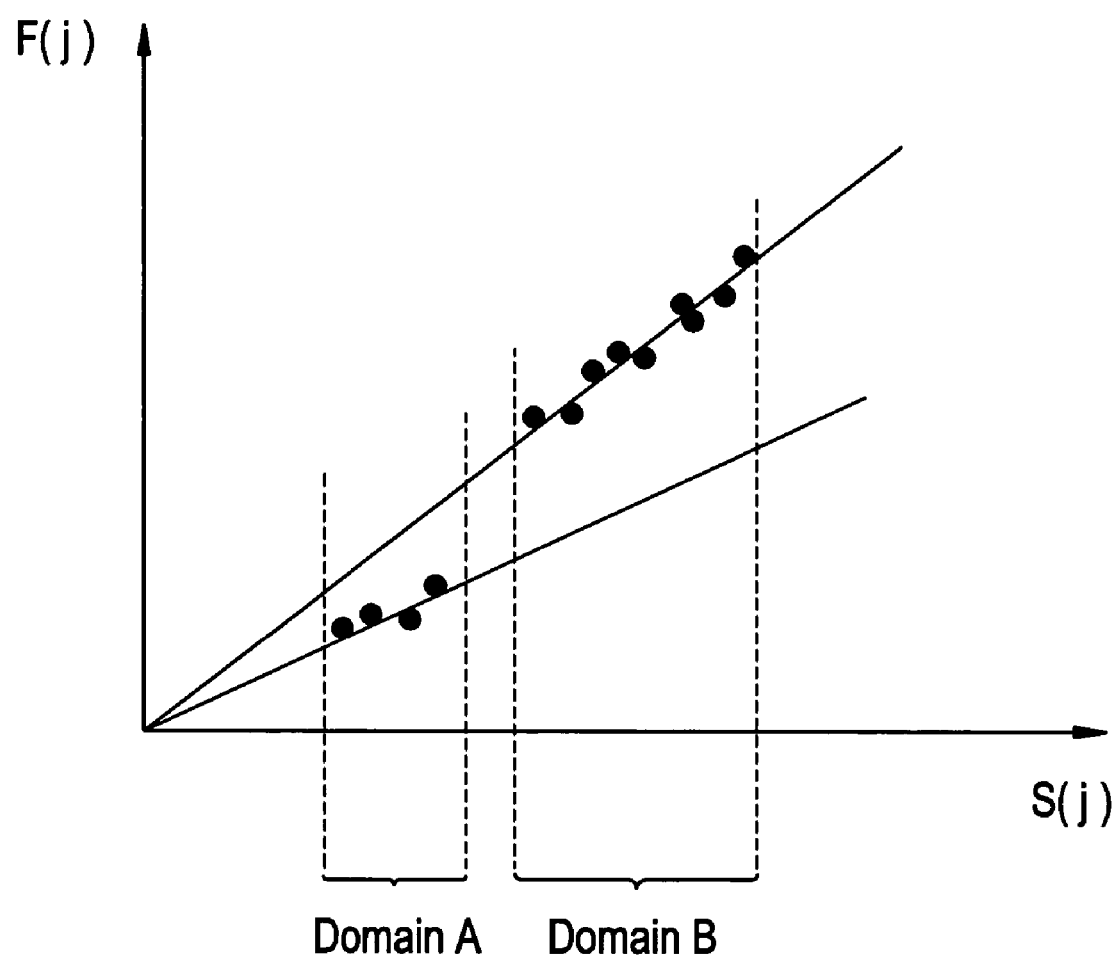

X-RAY CT SYSTEM AND BEAM-HARDENING POST-PROCESSING METHOD

CROSS REFERENCE TO RELATED APPLICATIONS

This application claims the benefit of Japanese Application No. 2003-112906 filed Apr. 17, 2003.

BACKGROUND OF THE INVENTION

The present invention relates to a beam-hardening post-processing method for correcting the intensity of X-rays to be transmitted by a subject on the basis of phantom data, and to an X-ray computed tomography (CT) system.

An X-ray source employed in an X-ray CT system generates X-rays that fall within a certain energy range. On the other hand, an absorption coefficient for X-rays transmitted by a subject depends on the energy in the X-rays. The larger a length in a subject over which X-rays are transmitted, the larger the average energy. This phenomenon is referred to as a beam-hardening effect. Consequently, a proportional relationship is not established between the intensity of transmitted X-rays, that is, a projection information value and the length over which X-rays are transmitted, but a non-linear relationship is.

The beam-hardening effect causes the cupping effect signifying that the intensity detected in the center of a reconstructed image is low. A correction coefficient to be used to correct projection information values based on which a reconstructed image is produced to exhibit a uniform intensity is calculated in relation to each of the channels of the X-ray detector, whereby the correction is achieved (refer to, for example, Patent Document 1).

A plurality of cylindrical phantoms having different diameters that are large enough to generally cover the entire field of view (FOV) (scan field) defined in the center of an X-ray field is scanned for the purpose of higher-precision correction. Projection information acquired from the phantoms is used to improve the precision in correction.

[Patent Document 1]
Japanese Unexamined Patent Publication No. Hei 5(1993)-130987 (p.2 and 3, FIG. 1 and FIG. 2)

By the way, for highly precise correction of projection information values, the largest possible number of different projection information values is needed in relation to each of the channels of an X-ray detector. Therefore, lots of phantoms that have different diameters must be scanned.

On the other hand, the larger the diameter of a phantom, the lower a signal-to-noise ratio reflected in an acquired projection information value. If a correction coefficient calculated from projection information values reflecting lowered signal-to-noise ratios is used to correct projection information, a reconstruction image is like to suffer degradation in image quality deriving from a ring artifact or the like. Consequently, when a subject having large dimensions is scanned, image quality is likely to be degraded.

SUMMARY OF THE INVENTION

An object of the present invention is to provide an X-ray CT system in which even when a subject having relatively large dimensions is scanned, projection data can be highly precisely corrected in terms of the beam-hardening effect in relation to each of the channels of an X-ray detector, and to provide a beam-hardening post-processing method for X-ray CT systems.

According to the present invention, there is provided an X-ray CT system in which: an X-ray detector having multiple channels is used to acquire projection information, which is provided by an X-ray beam passing through a scan field, as a plurality of views from plural directions; and projection information detected on each of the channels is corrected in terms of the beam-hardening effect. The X-ray CT system comprises: a correction coefficient producing means that calculates a correction coefficient, which is used for correction, from projection information acquired from a phantom placed in the scan field; a correction coefficient modifying means that uses a first correction coefficient, which the correction coefficient producing means calculates using projection information acquired from a first phantom, to modify a second correction coefficient which the correction coefficient producing means calculates using projection information acquired from a second phantom larger in dimensions than the first phantom; and a correcting means that corrects projection information, which is acquired from a subject positioned in the scan field, using the first correction coefficient and the corrected second correction coefficient.

Preferably, the correction coefficient producing means comprises: a producing means that samples first projection information from projection information acquired from a phantom in relation to all views so as to produce one sinogram; a beam-hardening correction means that corrects the first projection information in terms of the beam-hardening effect so as to produce second projection information; a first fitting means that fits a first function to the second projection information so as to produce third projection information; and a second fitting means that fits a second function to the third projection information values which are provided as functions having as independent variables the second projection information values sampled in relation to all the views and each of the channels of the X-ray detector.

More preferably, the X-ray detector is formed with a plurality of detection modules each having a predetermined number of channels. The correction coefficient modifying means separates the reflections of high-frequency components from correction coefficient data calculated using the second phantom so as to leave the dependencies on the detection characteristics of the detection modules. The correction coefficient modifying means then synthesizes the correction coefficient data, from which the reflections of high-frequency components are separated, with the reflections of high-frequency components in correction coefficient data calculated using the first phantom.

A beam-hardening post-processing method for X-ray CT systems in accordance with the present invention comprises: an acquiring step of scanning a first phantom and a second phantom, which is larger in dimensions than the first phantom, placed between an X-ray tube and an X-ray detector, and acquiring projection information as a plurality of views from plural directions using an X-ray detector that has multiple channels; a producing step of calculating first and second correction coefficients, which are used to correct the projection information detected on each of the channels of the X-ray detector, from projection information acquired from the first and second phantoms; a modifying step of modifying the second correction coefficient using the first correction coefficient; and a correcting step of correcting projection information, which is acquired from a subject positioned in the scan field, using the first correction coefficient and the modified second correction coefficient.

According to the present invention, the first phantom and the second phantom larger in dimensions than the first phantom are scanned in order to acquire projection information. The first and second correction coefficients that are used for correction are calculated from the projection information.

The larger the dimensions of a phantom, the lower a signal-to-noise ratio. Therefore, a CT image produced by performing correction using the second correction coefficient is more likely to suffer degradation in image quality attributable to a ring artifacts or the like than a CT image produced by performing correction using the first correction coefficient.

According to the present invention, the first correction coefficient calculated from projection information that reflects relatively high signal-to-noise ratios is used to modify the second correction coefficient.

Consequently, even when a correction coefficient is calculated using a phantom that has large dimensions, correction can be achieved highly precisely.

According to the present invention, the precision in correcting projection information acquired from a large subject can be improved.

Further objects and advantages of the present invention will be apparent from the following description of the preferred embodiments of the invention as illustrated in the accompanying drawings.

BRIEF DESCRIPTION OF THE DRAWINGS

FIG. 7 presents processing to be performed on projection information values in the direction of channels.

FIG. 12 is a graph presenting an example of correction coefficients calculated using two phantoms having different diameters.

DETAILED DESCRIPTION OF THE INVENTION

Referring to appended drawings, a preferred embodiment of a beam-hardening post-processing method and an X-ray CT system in accordance with the present invention will be described below.

Figure 1:
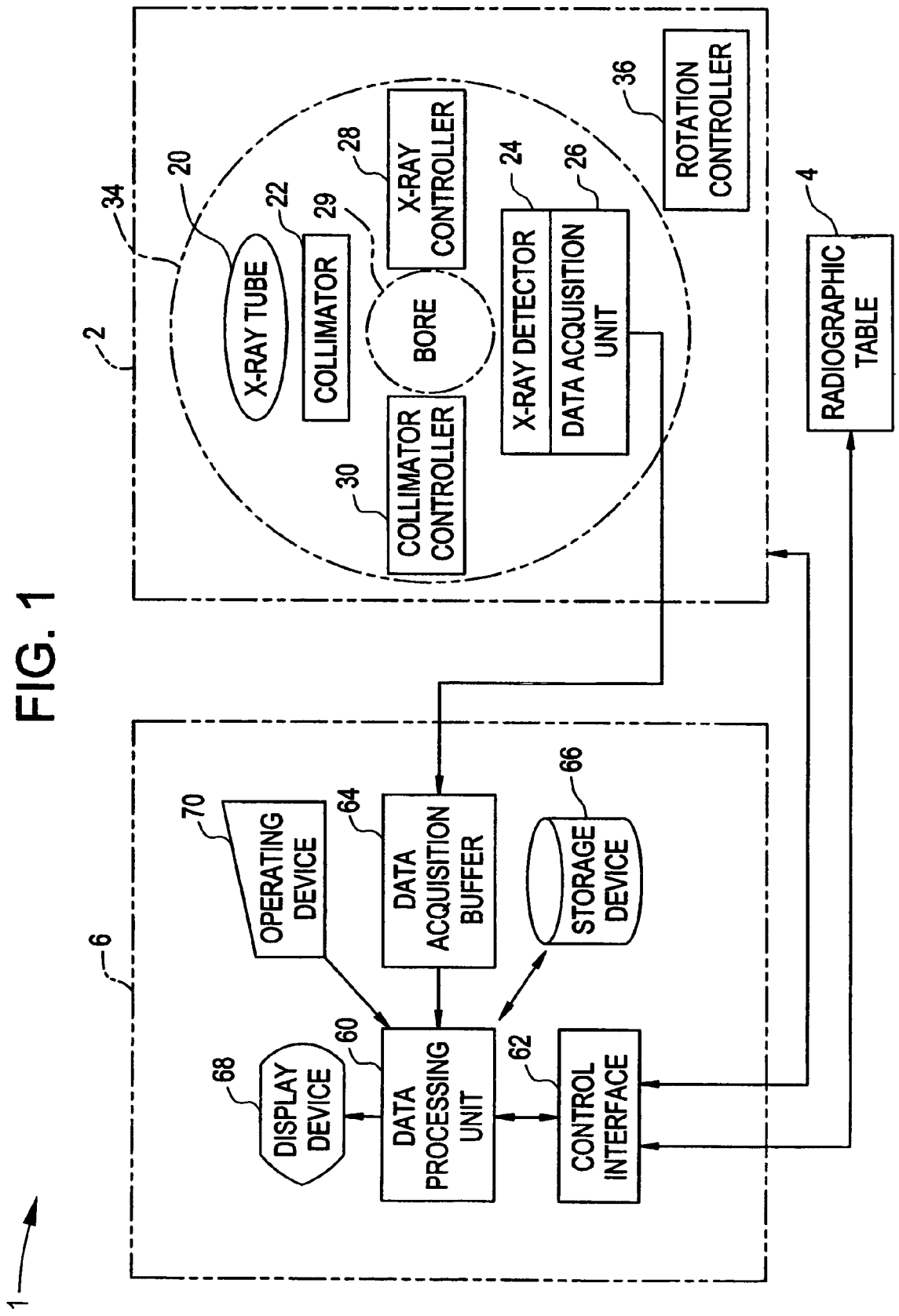
FIG. 1 is a block diagram showing the overall configuration of an X-ray CT system.

To begin with, the overall configuration of an X-ray CT system of an embodiment will be described below. FIG. 1 is a block diagram of an X-ray CT system 1. As shown in FIG. 1, the X-ray CT system 1 comprises a scanner gantry 2 and an operating console 6.

The scanner gantry 2 includes an X-ray tube 20. X-rays radiated from the X-ray tube 20 and not shown are recomposed into, for example, a fan-shaped X-ray beam, that is, fan-beam X-rays by means of a collimator 22, and then irradiated to an X-ray detector 24.

The X-ray detector 24 has a plurality of X-ray detection elements set in array in a direction in which the fan-beam X-rays spread. The X-ray detector 24 is therefore a multichannel detector having the plurality of X-ray detection elements set in array.

The X-ray detector 24 forms an X-ray incidence surface curved like a cylindrical concave surface as a whole. The X-ray detector 24 is formed using, for example, a combination of a scintillator and a photodiode. The present invention is not limited to this combination. For example, a semiconductor X-ray detection element that utilizes cadmium telluride (CdTe) or an ion-chamber type X-ray detection element that utilizes xenon gas will do. The X-ray tube 20, collimator 22, and X-ray detector 24 constitute an X-ray irradiation/detection unit.

A data acquisition unit 26 is connected to the X-ray detector 24. The data acquisition unit 26 acquires data items detected by the respective X-ray detection elements constituting the X-ray detector 24. An X-ray controller 28 controls X-irradiation from the X-ray tube 20. Illustrating the connective relationship between the X-ray tube 20 and X-ray controller 28 and the connective relationship between the collimator 22 and a collimator controller 30 will be omitted. The collimator controller 30 controls the collimator 22.

The foregoing components started with the X-ray tube 20 and ended with the collimator controller 30 are incorporated in a rotary assembly 34 of the scanner gantry 2. A subject or a phantom is mounted on a cradle within a bore 29 located in the center of the rotary assembly 34. The rotary assembly 34 is rotated while being controlled by a rotation controller 36. X-rays are irradiated from the X-ray tube 20. The X-ray detector 24 detects X-rays transmitted by the subject or phantom as projection information composed of views. Illustrating the connective relationship between the rotary assembly 34 and rotation controller 36 will be omitted.

The operating console 6 includes a data processing unit 60. The data processing unit 60 is realized with, for example, a computer. A control interface 62 is connected to the data processing unit 60, and the scanner gantry 2 is connected to the control interface 62. The data processing unit 60 controls the scanner gantry 2 via the control interface 62.

The data acquisition unit 26, X-ray controller 28, collimator controller 30, and rotation controller 36 which are incorporated in the scanner gantry 2 are controlled via the control interface 62. Illustrating the connections among these components and the control interface 62 will be omitted.

A data acquisition buffer 64 is also connected to the data processing unit 60. The data acquisition unit 26 incorporated in the scanner gantry 2 is connected to the data acquisition buffer 64. Data acquired by the data acquisition unit 26 is transferred to the data processing unit 60 via the data acquisition buffer 64.

The data processing unit 60 reconstructs an image using transmitted X-ray signals, that is, projection information transferred via the data acquisition buffer 64. A storage device 66 is also connected to the data processing unit 60. Projection information transferred via the data acquisition buffer 64, tomographic image information resulting from image reconstruction, and programs that realize the capabilities of the system are stored in the storage device 66.

A display device 68 and an operating device 70 are also connected to the data processing unit 60. Tomographic image information and other information transferred from the data processing unit 60 are displayed on the display device 68. An operator handles the operating device 70 so as to enter various instructions or information which is then transferred to the data processing unit 60. The operator uses the display device 68 and operating device 70 to interactively operate the X-ray CT system 1. Incidentally, the scanner gantry 2, a radiographic table 4, and the operating console 6 constitute an acquisition system that scans a subject or a phantom so as to acquire tomographic image data.

Figure 2:
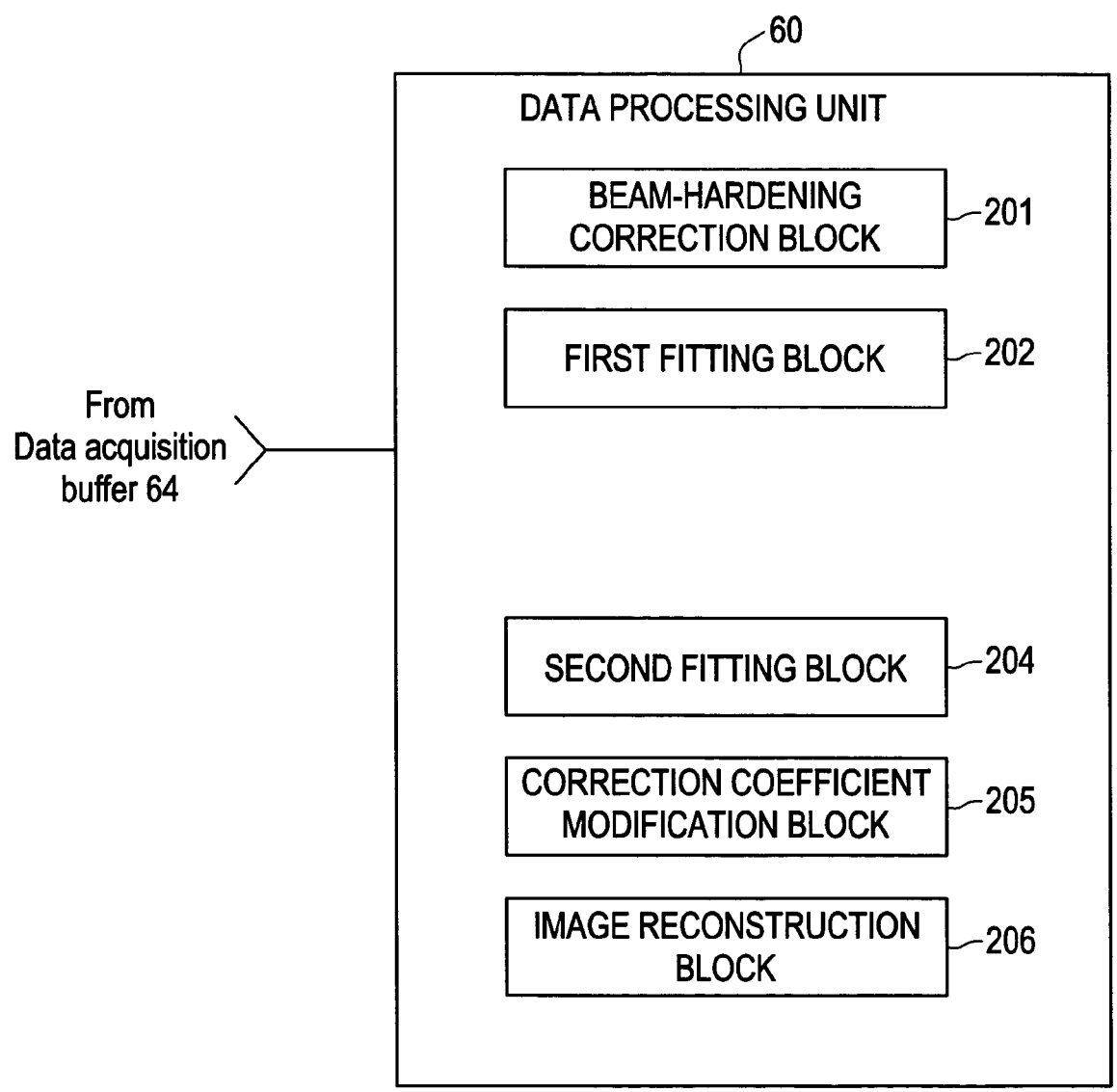
FIG. 2 is a functional block diagram showing a data processing unit.

FIG. 2 is a functional block diagram showing a portion of the data processing unit 60 relating to a beam-hardening post-processing method in accordance with the present embodiment.

The data processing unit 60 comprises a beam-hardening correction block 201, a first fitting block 202, a second fitting block 204, a correction coefficient modification block 205, and an image reconstruction block 206 which deal with projection information stored in the storage device 66.

The beam-hardening correction block 201 corrects projection information stored in the storage device 66 in terms of the beam-hardening effect. Assuming that projection information values detected on each of the channels of the X-ray detector 24 are Ih and data corrected in terms of the beam-hardening effect is IC, correcting projection information in terms of the beam-hardening effect is expressed as follows:

$$IC = B_0 \cdot Ih + B_1 \cdot Ih^2 + B_2 \cdot Ih^3 + B_3 \cdot Ih^4 \tag{1}$$

where $B_0$ to $B_3$ denote correction coefficients. These correction coefficients are finalized in relation to each of the channels of the X-ray detector according to a method described in, for example, Patent Document 1, and stored in the form of a correction coefficient table in the storage device 66.

The first fitting block 202 smoothes projection information values, which are sampled in relation to all the respective views and each channel or which are sampled in relation to each view and all the respective channels, from projection information stored in the storage device 66. The first fitting block 202 averages the projection information values that are sampled in relation to each channel and all the respective views or that are sampled in relation to all the respective channels and each view. Otherwise, the first fitting block 202 fits a high-order function to the projection information values sampled in the direction of channels or in the direction of views so as to average the projection information values.

A function resulting from the fitting does not reflect high-frequency components of acquired signals that are higher than frequency components determined with the order of the function. The fitting therefore provides the same effect as smoothing.

The second fitting block 204 fits a linear or high-order function to projection information values which are detected on each of the channels of the X-ray detector 24 and to which the first function is fitted by the first fitting block 202. This results in the same correction coefficients as the ones provided by the expression (1) solved by the beam-hardening correction block 201.

The correction coefficient modification block 205 modifies the correction coefficient, which the second fitting block 204 has just calculated as a function, using a correction coefficient which the second fitting block 204 has already calculated as a function using projection information acquired from other phantom, if necessary (if the diameter of the phantom is so large that projection information reflects low signal-to-noise ratios). A concrete process will be described later.

The image reconstruction block 206 uses a sinogram, which is produced using projection information composed of a plurality of views and stored in the storage device 66, to reconstruct a tomographic image of a subject or a phantom. For image reconstruction, for example, the filtered back projection technique is adopted. A reconstructed image is displayed on the display device 68.

Figure 3:
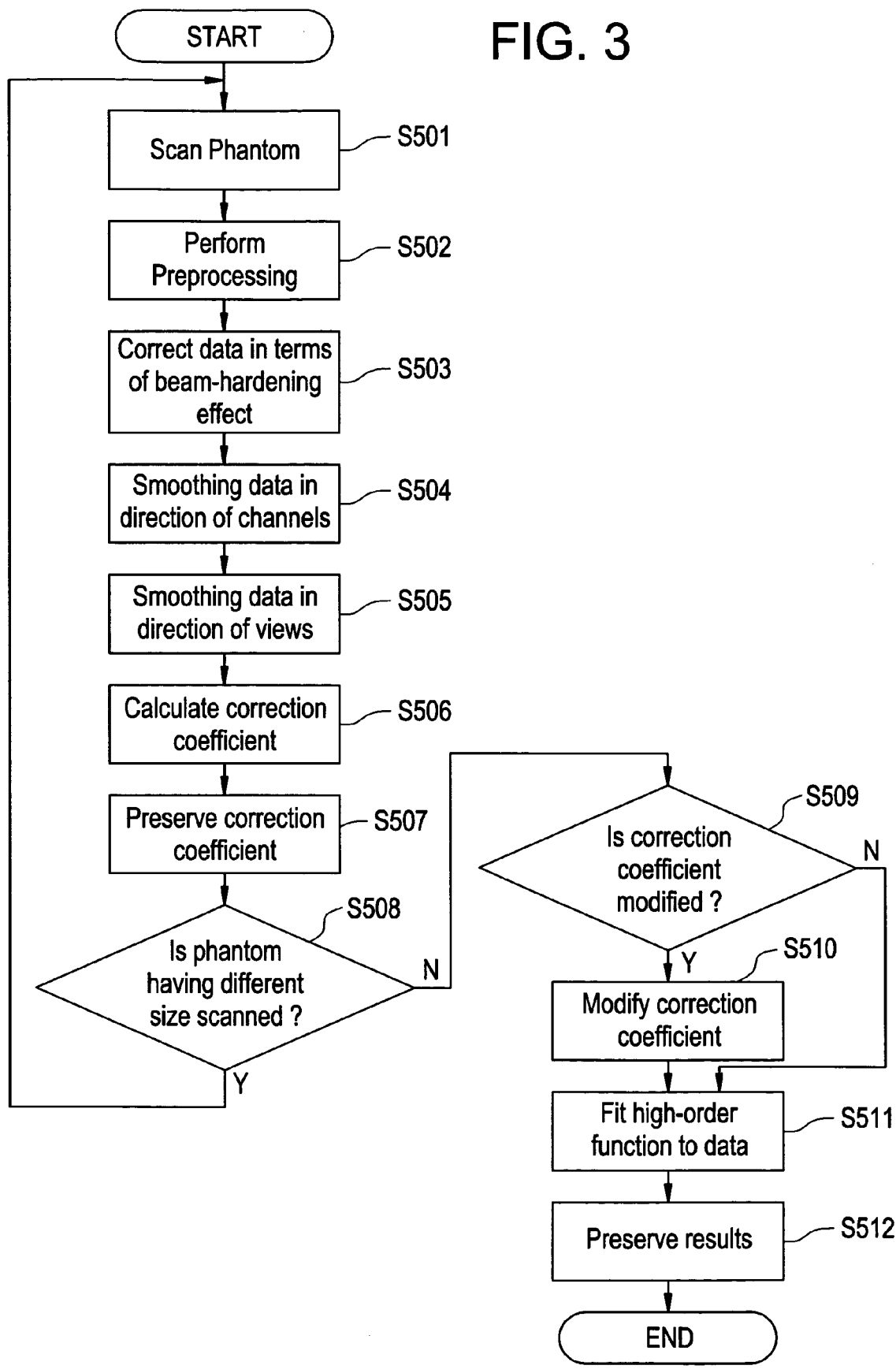
FIG. 3 is a flowchart describing actions to be performed in the data processing unit.

Next, an example of a procedure for calculating a correction coefficient needed for correction that is performed as post-processing in order to cope with the beam-hardening effect in the X-ray CT system 1 will be described with reference to the flowchart of FIG. 3.

Scanning a Phantom

First, a phantom is scanned (step S501). Specifically, a phantom is disposed at a position off the center of the X-ray field in the bore 29. The phantom is made of a polypropylene or the like and shaped like a cylinder. Phantoms having various diameters are available. The present embodiment employs phantoms whose diameters are 35 cm and 48 cm. The phantoms whose diameters are 35 cm and 48 cm are scanned in that order.

When a phantom is scanned, the phantom is disposed at a position off the center of the X-ray field in the bore 29. This is because the length of a path traced by X-rays transmitted by the phantom can be differentiated from view to view. In order to highly precisely correct projection information values in terms of the beam-hardening effect, the largest possible number of different projection information values is needed in relation to each channel. When a phantom is disposed at a position off the center of the X-ray field in the bore 29, numerous different projection information values can be acquired from one phantom.

Figure 4:
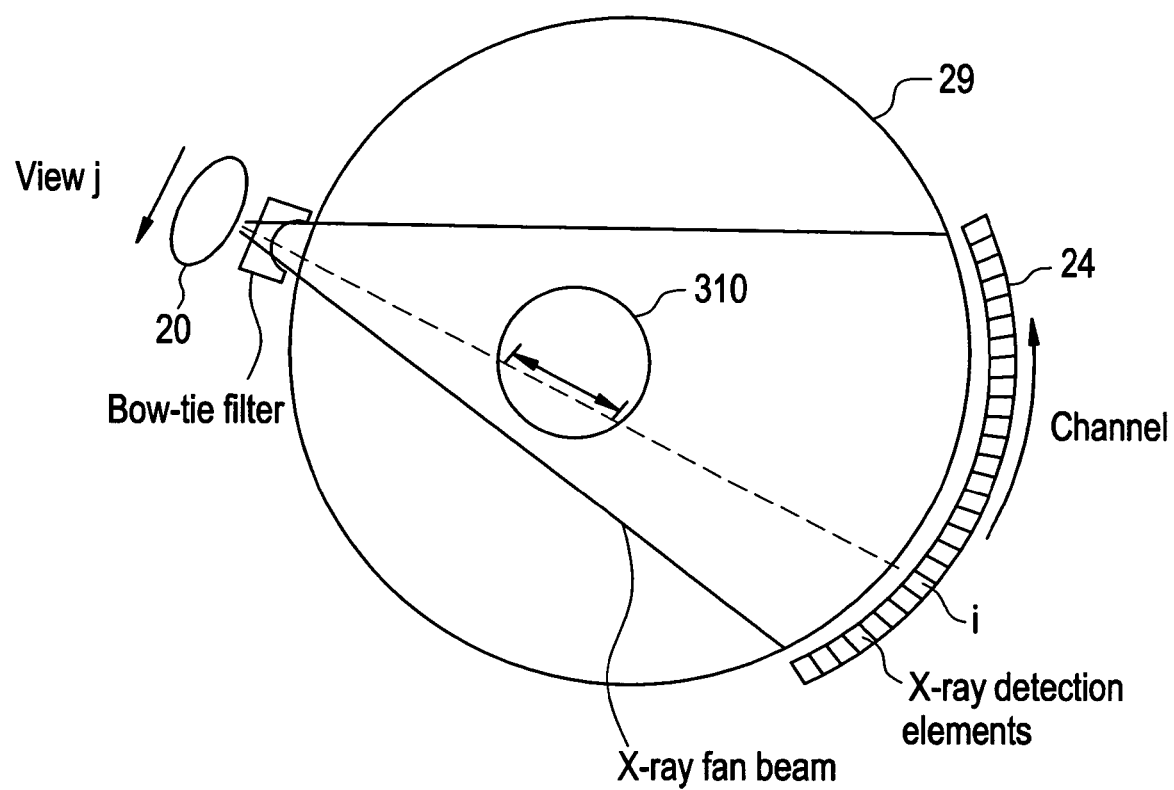
FIG. 4 shows an embodiment of a positional relationship between a phantom and a rotary assembly.

FIG. 4 shows a phantom 310 disposed in the bore 29 of the scanner gantry 2.

The phantom 310 has a circular section, and the center of the phantom 310 is located at a position different from the center of the X-ray field in the bore 29. An X-ray fan beam into which X-rays generated by the X-ray tube 20 are recomposed by a bow-tie filter is transmitted by the phantom 310 and detected by the X-ray detector 24.

The X-ray detector 24 has a plurality of X-ray detection elements set in array in a direction in which the X-ray fan beam spreads. Projection information acquired from the phantom 310 is detected on the channels assigned to the X-ray detection elements set in array. Herein, the X-ray tube 20 and collimator 22 are opposed to the X-ray detector 24 with the bore 29 between them. The X-ray tube 20, collimator 22, and X-ray detector 24 are rotated about the bore 29 without any change in their relative positions while being incorporated in the rotary assembly 34, whereby projection information is acquired. Projection information is acquired for each view number associated with a rotation angle, and one sinogram is produced.

Figure 5A:
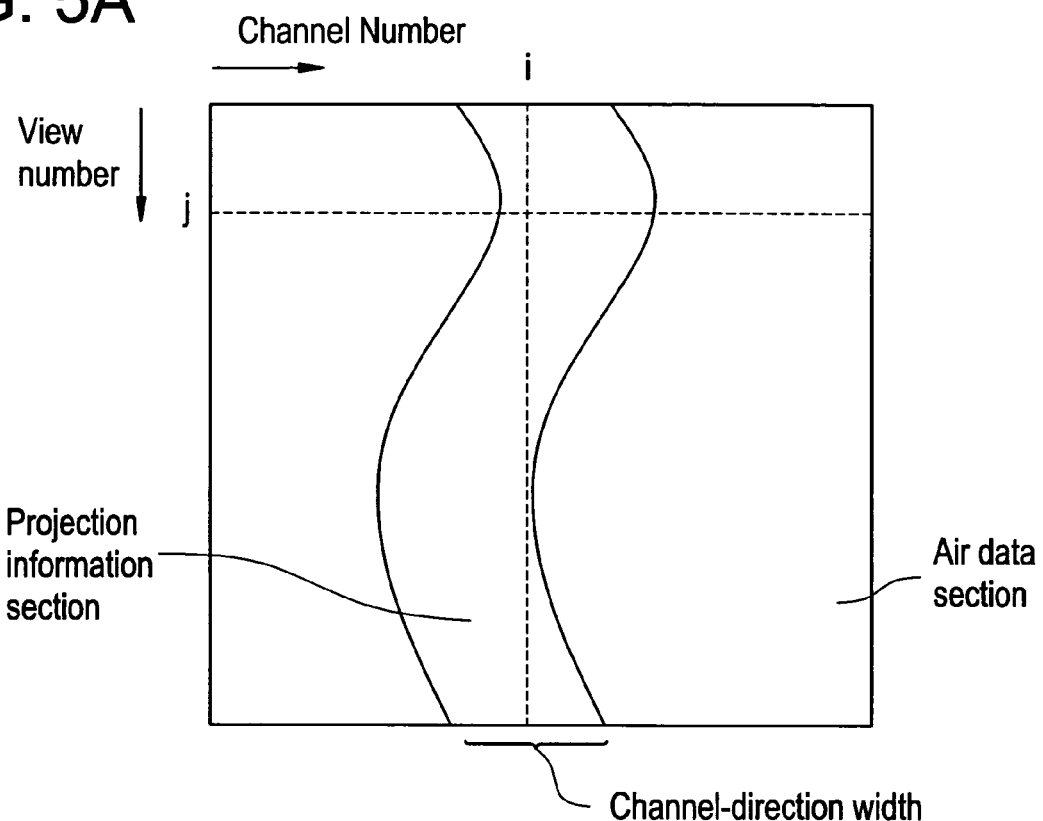
FIG. 5 shows an embodiment of a sinogram produced from projection information values acquired from a phantom, and the projection information values.

FIG. 5(A) shows an example of a sinogram produced using the phantom 310. The sinogram comprises a projection information section defined around the center of one dimension of the sinogram associated with channel numbers, and an air data section defined on both sides of the projection information section along the dimension associated with channel numbers. The phantom 310 is disposed off the center of the X-ray field. Therefore, the channel numbers determined with the channel-direction width of the projection information section vary with a change in the rotation angle of the rotary assembly 34, that is, a change in the view number. As shown in FIG. 5(A), the projection information section is tortuous in the direction of view numbers. For the same reason, the channel-direction width of the projection information section varies with a change in the view number.

Figure 5B:
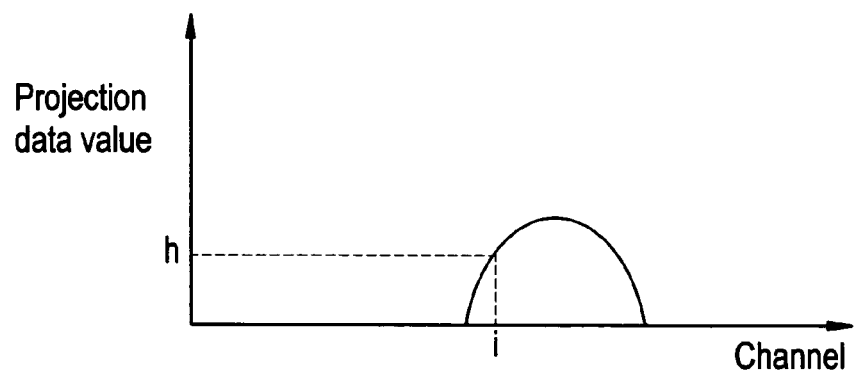

FIG. 5(B) is a graph whose axis of abscissas indicates channel numbers and whose axis of ordinates indicates projection information values, wherein projection information of view number j indicated in FIG. 5(A) is pointed out. The projection information value is proportional to a length in the phantom 310 over which an X-ray beam is transmitted. X-rays passing through near the center of the phantom 310 are transmitted over a slarge length and provide large projection information values. X-rays passing through near the periphery of the phantom 310 are transmitted over a small length and provide small projection information values based on which a semi-circular projection image like the one shown in FIG. 5(B) is displayed.

Now, a projection information value indicated with view number j and channel number i will be taken for instance. An X-ray beam indicated with a dashed line in FIG. 4 provides a view of view number j and falls on a channel of channel number i of the X-ray detector 24. At this time, a length in the phantom 310 over which the X-ray beam is transmitted shall be 1. The length l and a projection information value h detected on channel i and indicated in FIG. 5(B) has the relationship expressed below.

$$l \propto h$$

Referring to FIG. 4, the phantom 310 is located at a position off the center of the X-ray field. The length l over which the X-ray beam is transmitted and routed to the channel varies depending on a view. Consequently, the projection information value h detected on the channel i and indicated in FIG. 5(B) varies depending on a view.

Figure 5C:
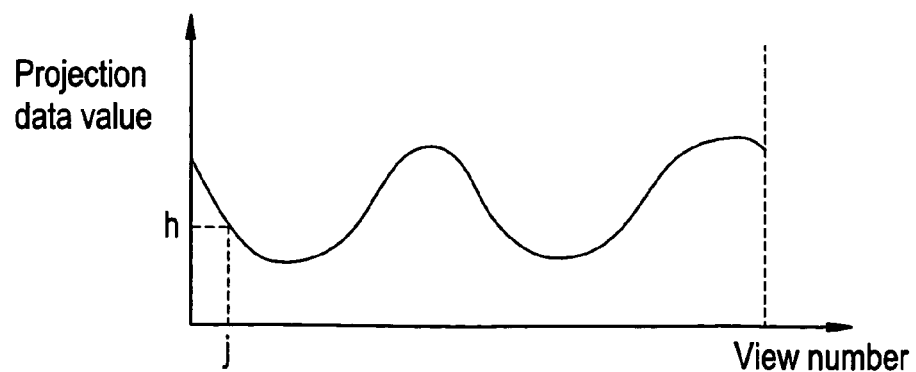

FIG. 5(C) is a graph whose axis of abscissas indicates view numbers and whose axis of ordinates indicates projection information values, wherein a projection information value detected on the channel of channel number i indicated in FIG. 5(A) is pointed out. The projection information value varies depending on a view number, and is proportional to a length in the phantom 310 over which an X-ray beam is transmitted. Therefore, the projection information value is provided as a function represented by a curve having cyclicity as shown in FIG. 5(C).

Figure 6:
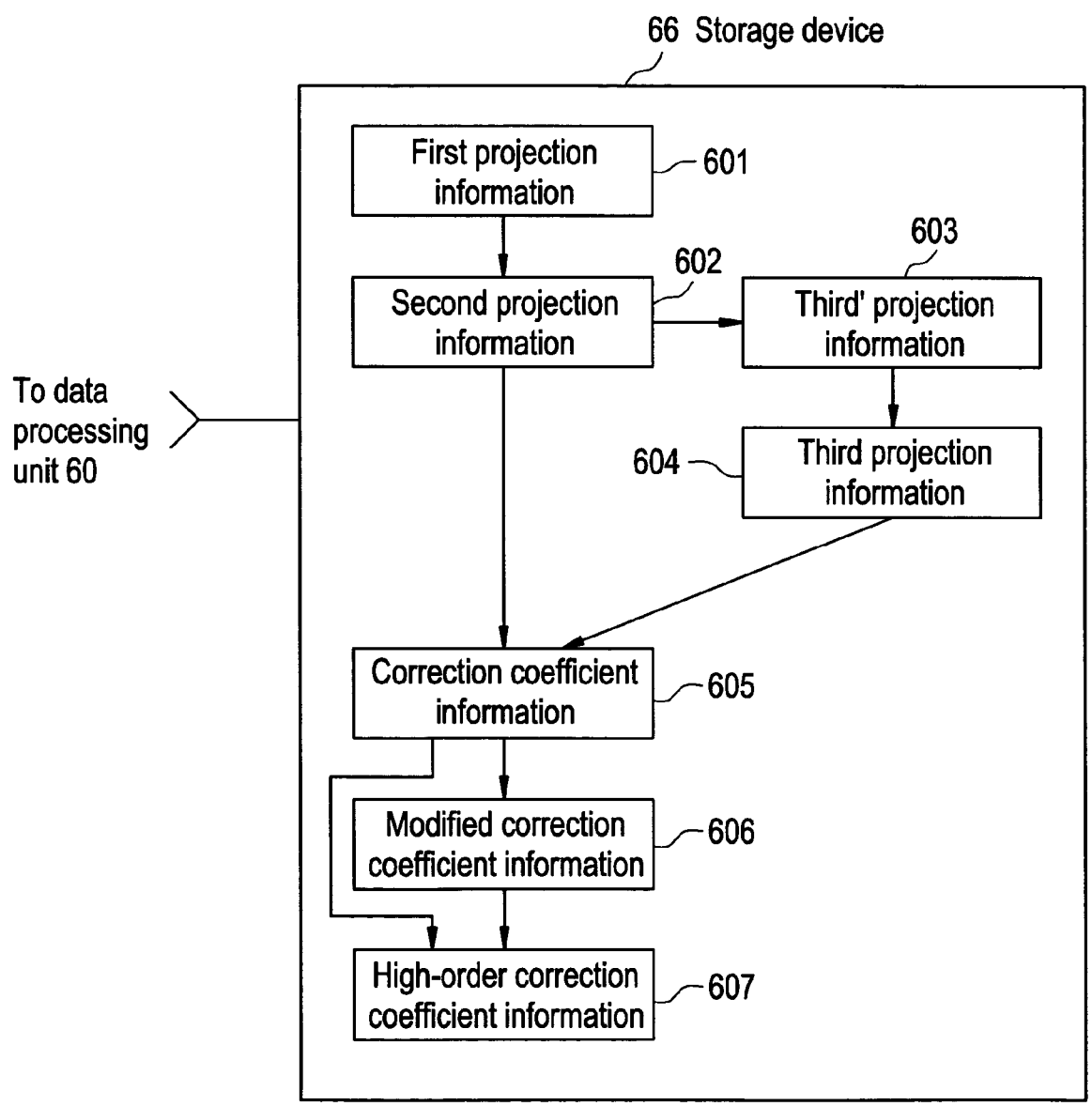
FIG. 6 is a block diagram showing files stored in a storage device.

FIG. 6 is a block diagram showing files stored in the storage device 66.

By scanning the phantom as mentioned above, first projection information 601 shown in FIG. 6 is acquired.

Preprocessing

Thereafter, a sinogram produced by scanning the phantom is preprocessed (step S502).

The preprocessing is performed on the sinogram produced from the first projection information, and includes noise removal and sensitivity correction.

Correcting Data in Terms of the Beam-hardening Effect

Thereafter, using the expression (1), the projection information values Ih are corrected in terms of the beam-hardening effect in order to produce corrected projection information values Ic (step S503).

Consequently, second projection information 602 shown in FIG. 6 is produced. This file has the beam-hardening effect generally removed from it. However, the beam-hardening effect slightly remains because of a difference of each channel of the X-ray detector 24 from the others.

FIG. 7(A) illustratively shows an example of the second projection information 602. The second projection information 602 is plotted generally semi-circularly because it is acquired from a phantom having a circular section. The projection information values Ic sampled in relation to some channels are plotted as pulse-like fluctuations because of a difference in the sensitivity to X-rays of each channel from the others. This is a phenomenon inherent to a channel, and must therefore be corrected in relation to each channel.

Figure 8A:
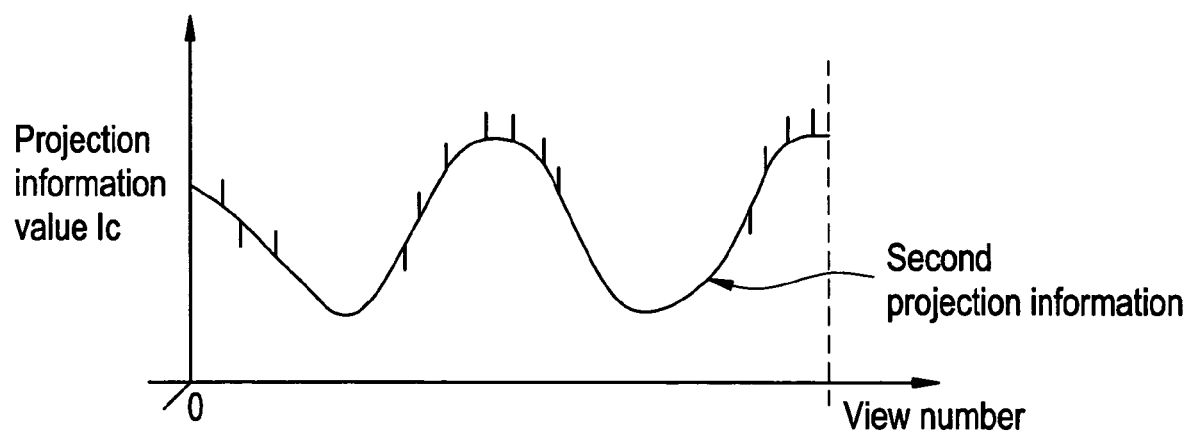
FIG. 8 presents processing to be performed on projection information values in the direction of views.

FIG. 8(A) illustratively shows an example of projection information values sampled from the second projection information 602 in the direction of views in relation to one channel. The projection information values Ic sampled in relation to some views are plotted as pulse-like fluctuations.

Smoothing in the Direction of Channels

Thereafter, the first fitting block 202 smoothes the second projection information 602 in the direction of channels (step S504).

Consequently, third' projection information 603 shown in FIG. 6 is produced. The third' projection information 603 has the projection information values Ic, which are plotted as fluctuations deriving from a difference of one channel from the others, smoothed and removed. FIG. 7(B) illustratively shows an example of the third' projection information 603. A semi-circular curve alone is plotted with the projection information acquired from a phantom having a circular section.

Smoothing in the Direction of Views

Thereafter, the first fitting block 202 smoothes the third' projection information 603 in the direction of views (step S505).

Consequently, third projection information 604 shown in FIG. 6 is produced. The third projection information 604 has projection information values, which are plotted as fluctuations deriving from a difference of one view from the others detected on one channel, smoothed.

Figure 8B:
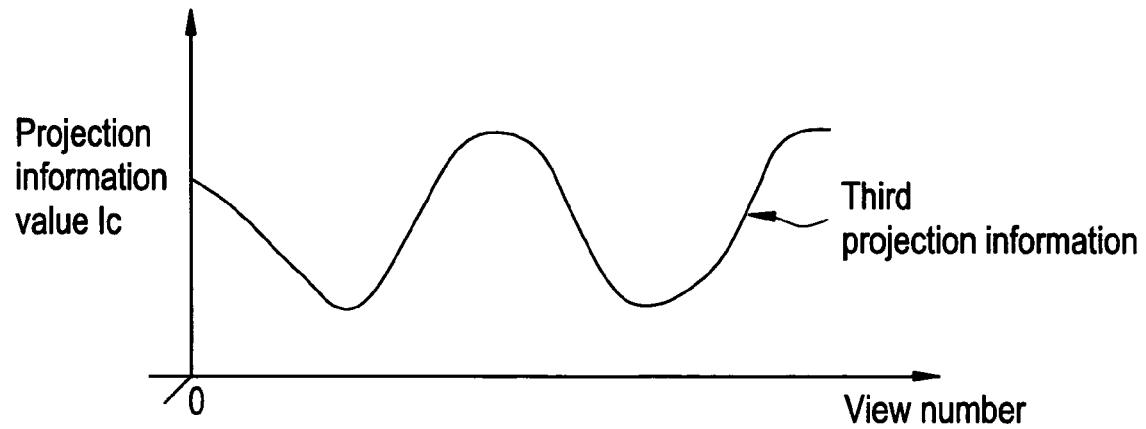

FIG. 8(B) illustratively shows an example of the third projection information. The projection information values that are sampled in relation to one channel in the direction of views and that exhibit cyclicity are smoothed.

Calculating a Correction Coefficient

Thereafter, the second fitting means 204 calculates a correction coefficient using the second projection information 602 and third projection information 603 (step S506).

Figure 9:
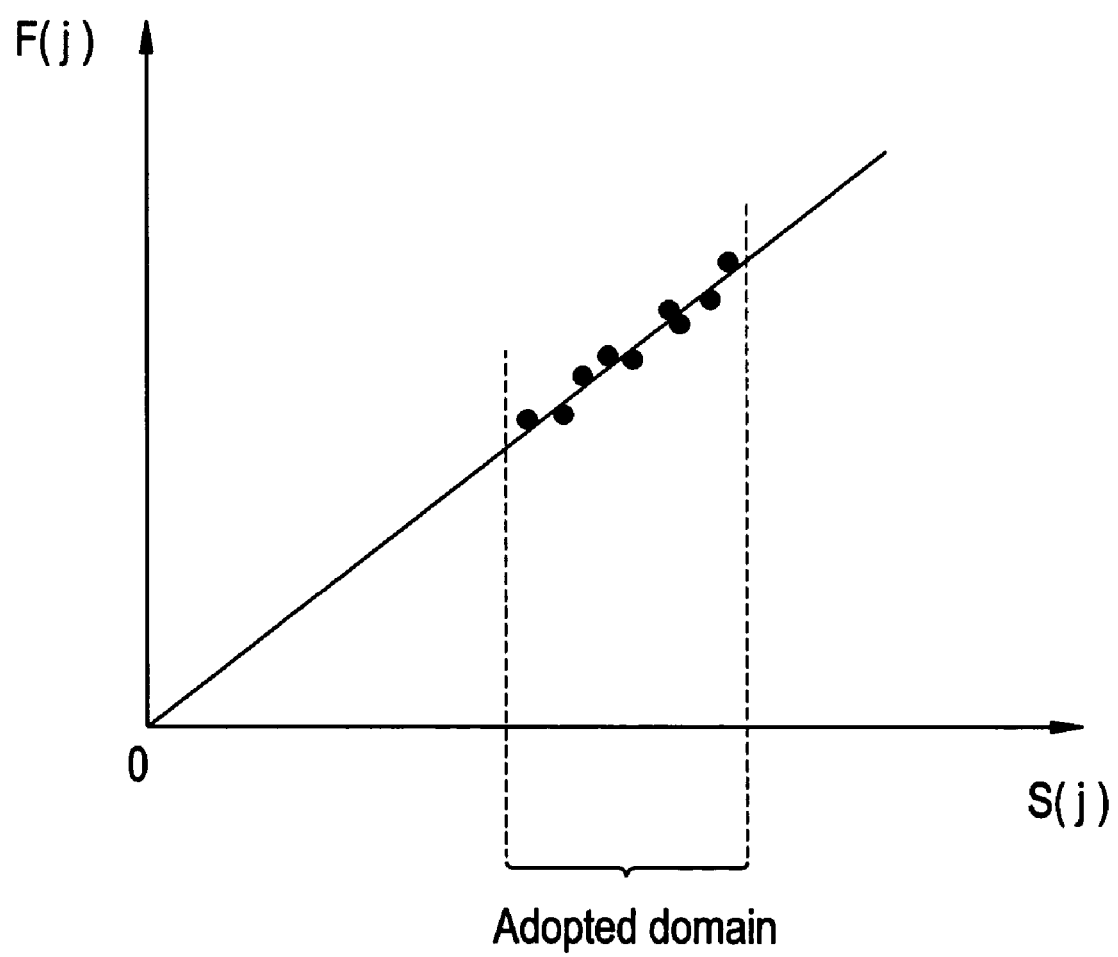
FIG. 9 shows an example of a correction coefficient calculated from projection information values.

Herein, projection information values sampled from the second projection information in relation to channel number i shall be S(j) and projection information values sampled from the third projection information in relation thereto shall be F(j). FIG. 9(A) indicates the projection information values sampled in relation to all the view numbers, wherein the axis of abscissas indicates the projection information values S(j) and the axis of ordinates indicates the projection information values F(j). The projection information values are generally plotted alone a straight line that passes an origin. The straight line represents a correction function relevant to the channel i. Assuming that the slope of the straight line is $K_1i$, $K_1i$ is regarded as correction coefficient information 605 shown in FIG. 6. Incidentally, S(j) and F(j) have the relationship expressed below.

$$F(j)/S(j) \ne Ki$$

The projection information values Ic sampled in relation to channel i from projection information that is acquired from a subject and that is corrected in terms of the beam-hardening effect are multiplied by the correction coefficient Ki of a linear function. Consequently, projection information values Ip are produced as projection information values that have been smoothed and corrected after being acquired from the subject.

The projection information values S(j) are proportional to the length l over which X-rays are transmitted and which is indicated in FIG. 4. Therefore, the projection information values S(j) and the adopted domain depend on the diameter of the phantom 310 and the position of the phantom in the bore 29.

Thereafter, the correction coefficient Ki is preserved as correction coefficient information 605 in the storage device 66 (step S507).

Thereafter, it is determined whether a phantom having a different size is scanned in order to acquire data (step S508).

For example, after a phantom having a diameter of 35 cm is scanned in order to produce correction coefficient information, if a phantom having a diameter of 48 cm should be scanned in order to produce correction coefficient information, the phantom having a diameter of 48 cm is disposed in the X-ray CT system 1. The foregoing steps S501 to S507 are then resumed.

Figure 10A:
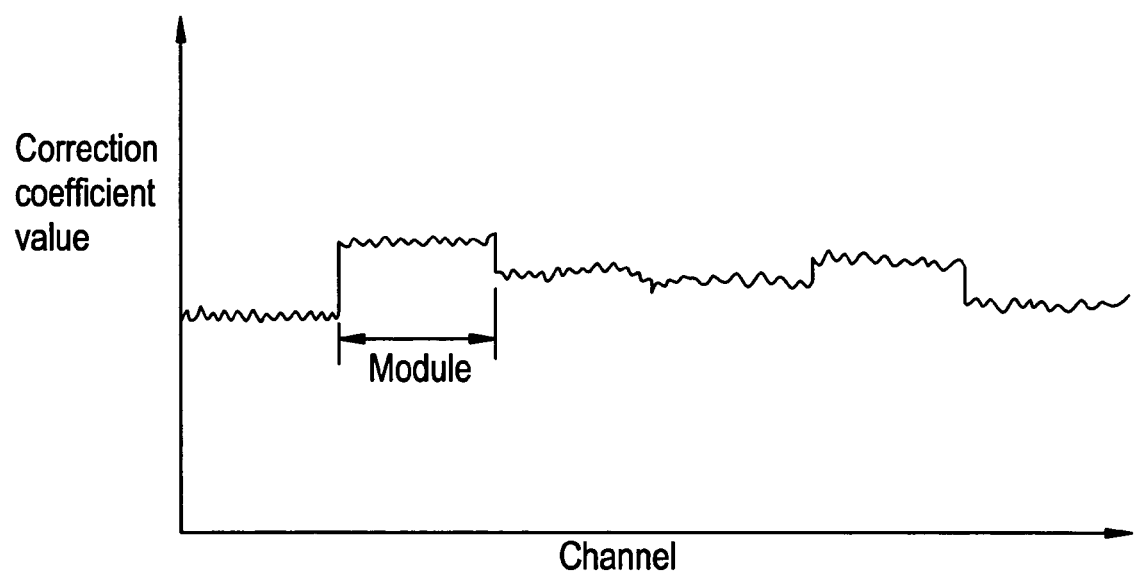
FIG. 10 shows examples of correction coefficients calculated from projection information values acquired from phantoms having different diameters.
Figure 10B:
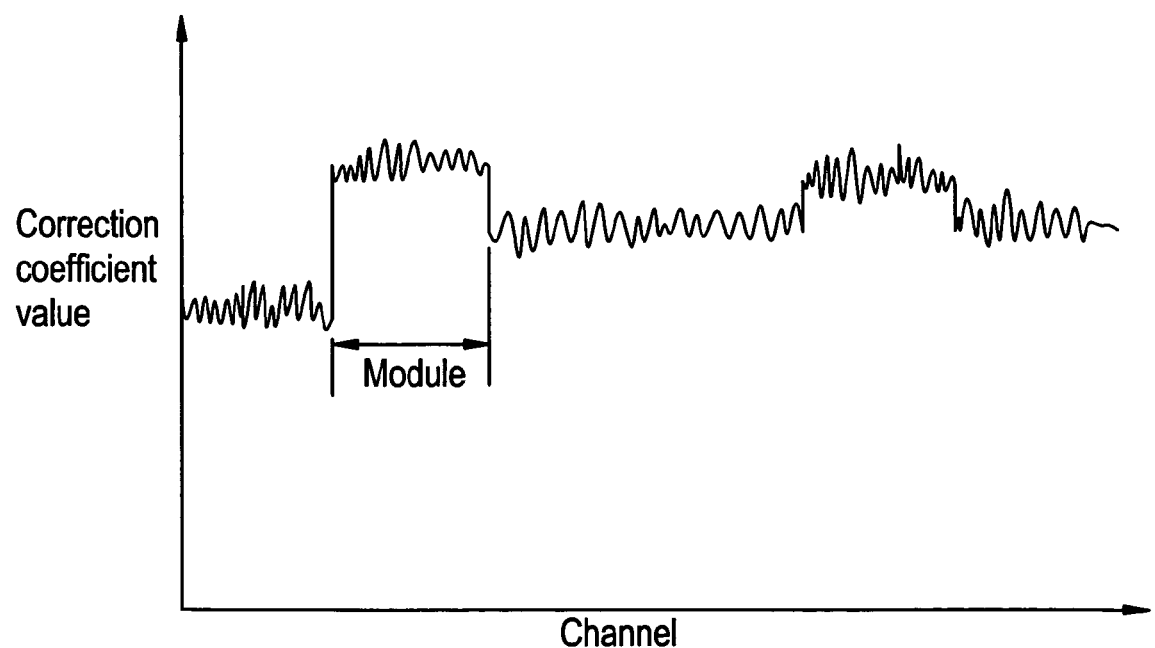

FIG. 10 is a graph indicating an example of the correction coefficient information 605 produced in relation to each channel. FIG. 10(a) indicates correction coefficients calculated using the phantom having a diameter of 35 cm, and FIG. 10(b) indicates corection coefficients calculated using the phantom having a diameter of 48 cm.

The correction coefficients calculated using the phantoms whose diameters are 35 cm and 48 cm are plotted as similar characteristic curves in relation to the channels. However, the correction coefficients calculated using the phantom having a diameter of 48 cm assume larger values.

The X-ray detector 24 comprises a plurality of detection modules each assigned a predetermined number of channels. The detection modules are manufactured as united bodies in units of sixteen channels. In other words, a predetermined number of detection modules each assigned sixteen channels is arrayed in order to construct the X-ray detector 24.

Therefore, the values detected on the channels within the same detection module reflect similar detection characteristics. In other words, the detection modules exhibit different detection characteristics.

Due to the above characteristics of the X-ray detector 24, the correction coefficient values arranged orderly in relation to the channels as shown in FIG. 10(a) and FIG. 10(b) contain the dependencies on the detection characteristics of the modules.

Moreover, as seen from FIG. 10(a) and FIG. 10(b), the correction coefficient values arranged orderly in relation to the channels contain the reflections of high-frequency components that depend on the detection characteristics of the respective channels.

The larger the diameter of a phantom, the lower the signal-to-noise ratios reflected in projection information detected by the X-ray detector 24. Besides, the precision in projection information detected on each channel gets lower. The reflections of high-frequency components in the correction coefficient values indicated in FIG. 10(b) include more reflections of noises than the reflections thereof in the correction coefficient values indicated in FIG. 10(a).

Therefore, when the correction coefficients calculated using, for example, the phantom having a diameter of 48 cm are adopted as they are, a reconstructed image may suffer a defect such as a ring artifact.

Modifying a Correction Coefficient

After the correction coefficient information 605 is produced using the phantom having a diameter of 48 cm by performing the steps S501 to S507, it is judged whether the correction coefficient information 605 should be modified (step S509).

At this time, the correction coefficient information 605 reflecting low signal-to-noise ratios as indicated in FIG. 10(b) is modified in S510. Correction coefficient information produced using the phantom having a small diameter of 35 cm is not modified.

FIG. 11 includes graphs for explaining an example of a method of modifying correction coefficient information 605.

Figure 11A:
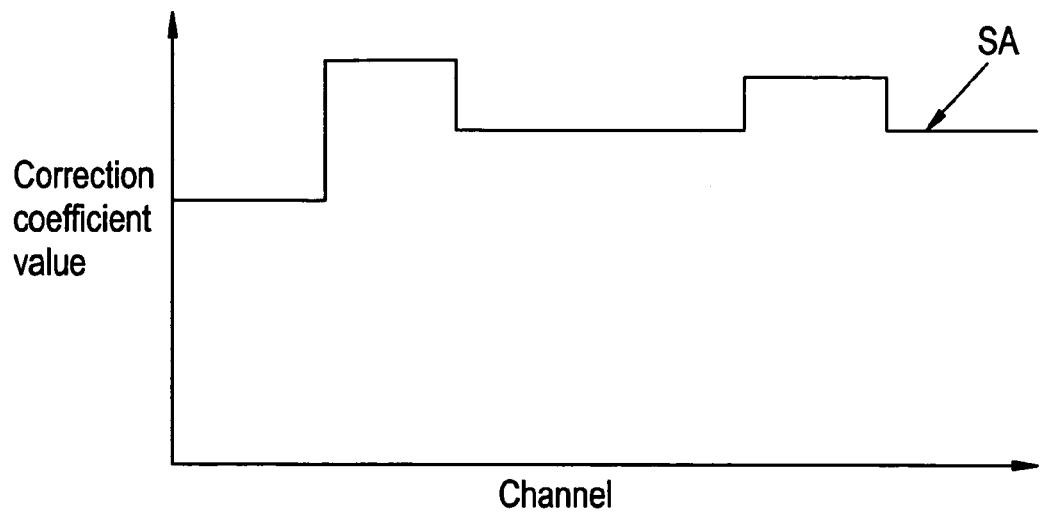
FIG. 11 includes graphs for explaining an example of a method of modifying correction coefficient information.

Referring to FIG. 11(a), SA indicates correction coefficients obtained by removing the reflections of high-frequency components from the correction coefficients that are calculated using the phantom having a diameter of 48 cm and indicated in FIG. 10(b).

The correction coefficients SA contain the dependencies on the detection characteristics of the detection modules but do not contain the reflections of high-frequency components that depend on the detection characteristics of the channels and that degrade signal-to-noise ratios.

Figure 11B:
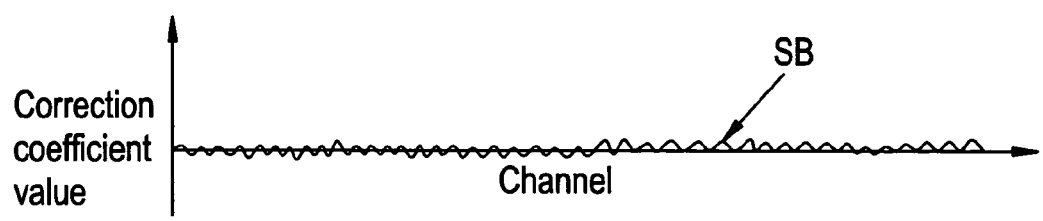

Referring to FIG. 11(b), a wave SB indicates the reflections of high-frequency signal components separated from the correction coefficients that are calculated using the phantom having a diameter of 35 cm and indicated in FIG. 10(a).

The wave SB indicates the reflections of high-frequency signal components in the correction coefficients that are calculated using the phantom having a diameter of 35 cm and that depend on the detection characteristics of the respective channels. The reflections of high-frequency components contain the reflections of noises at a smaller ratio than the reflections of high-frequency components in the correction coefficients calculated using the phantom having a diameter of 48 cm.

Figure 11C:
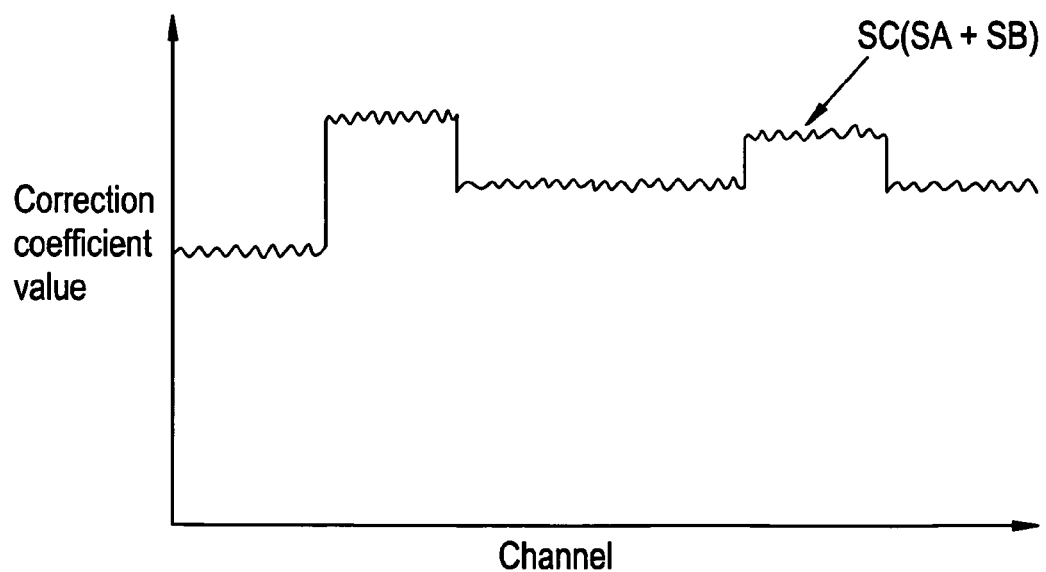

During modification of correction coefficient information 605 employed in the present embodiment, as indicated in FIG. 11(c), the correction coefficients SA from which the reflections of high-frequency components are removed are synthesized with the reflections of high-frequency components in the correction coefficients calculated using the phantom having a diameter of 35 cm. The resultant correction coefficients are adopted as new correction coefficients SC.

This results in the improved precision in correction coefficient information calculated using the phantom having a diameter of 48 cm. As shown in FIG. 6, the modified correction coefficient information is stored as modified correction coefficient information 606 in the storage device 66.

FIG. 12 shows an example of correction coefficients calculated using two phantoms having different diameters (35 cm and 48 cm).

Referring to FIG. 12, domain A comprises projection information values acquired from the phantom having a diameter of 35 cm, and domain B comprises projection information values acquired from the phantom having a diameter of 48 cm.

Fitting a High-order Function

Thereafter, a high-order function is fitted to a correction coefficient calculated using the phantom having a diameter of 35 cm and a correction coefficient calculated using the phantom having a diameter of 48 cm (step S511).

Figure 13:
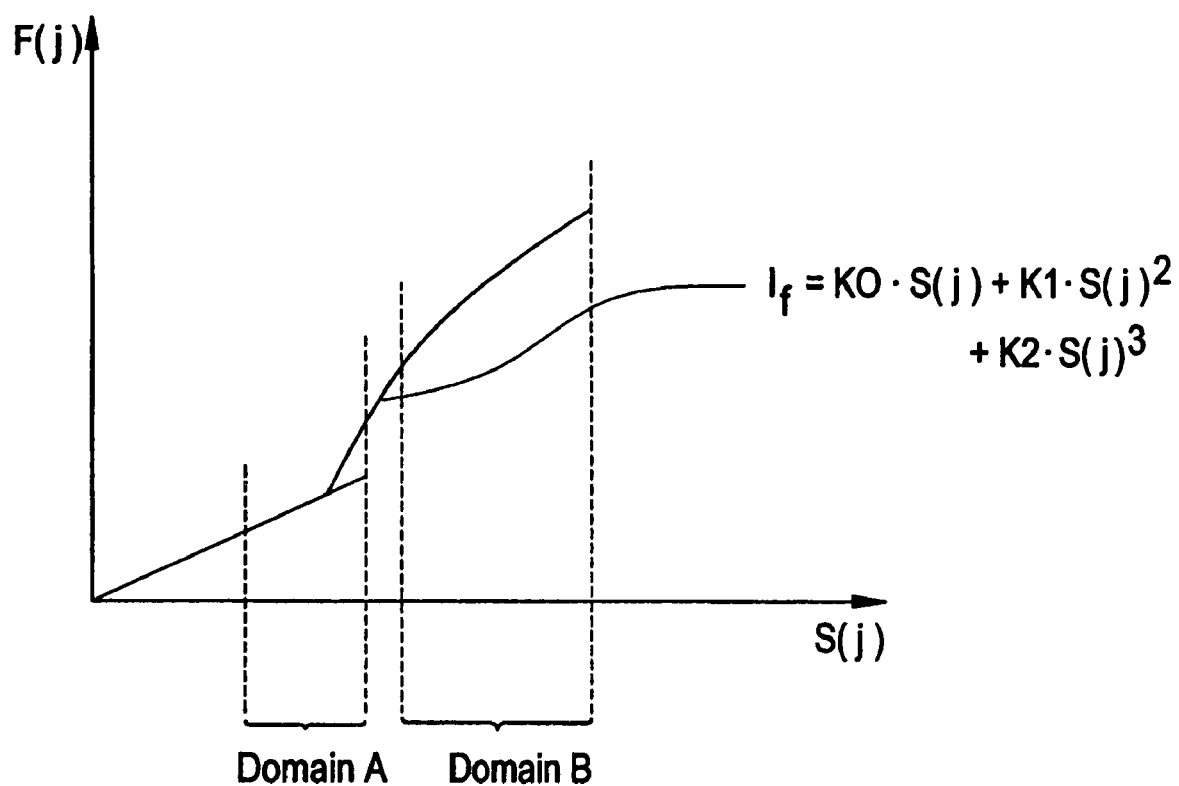
FIG. 13 is a graph presenting an example of fitting of a high-order function.

FIG. 13 shows an example of fitting of a high-order function performed using the correction coefficient information indicated in FIG. 12.

A third-order function given as expression (2) below is fitted to the correction coefficient value calculated from domain A and the correction coefficient value calculated from domain B, whereby correction coefficients K0, K1, and K2 are determined.

$$If = K0 \cdot S(j) + K1 \cdot S(j)^2 + K2 \cdot S(j)^3 \qquad (2)$$

Incidentally, the correction coefficient calculated from domain A composed of small projection information values is thought to be more highly precise than the correction coefficient calculated from domain B composed of large projection information values. Therefore, weights may be applied to the respective domains so that the third-order function will be more highly precisely fitted to the correction coefficient calculated from the domain A, and the correction coefficients in the expression (2) may then be determined.

Therefore, as shown in FIG. 6, high-order correction function information 607 containing the correction coefficients K0, K1, and K2 is preserved in the storage device 66 (step S512). The process is then terminated.

When a subject is scanned, projection information values Ic acquired from the subject and corrected in terms of the beam-hardening effect are corrected using correction coefficients K0, K1, and K2 that are calculated in relation to each channel. Corrected projection information values If are then calculated according to the expression (2). Based on the projection information values If, the image reconstruction block 206 reconstructs an image so as to acquire tomographic image information.

As mentioned above, according to the present embodiment, correction coefficient information that is calculated using a large phantom and that reflects low signal-to-noise ratios is corrected using correction coefficient information that is calculated using a phantom smaller than the phantom and that reflects high signal-to-noise ratios. Consequently, projection information values corrected in terms of the beam-hardening effect and sampled in relation to each channel can be corrected highly precisely.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT system in which an X-ray detector having multiple channels is used to acquire projection information, which is provided by an X-ray beam having passed through a scan field, as a plurality of views from plural directions, and projection information detected on each of the channels is corrected in terms of a beam-hardening effect, comprising:

a correction coefficient producing device for acquiring projection information from a phantom disposed in the scan field, and calculating a correction coefficient, which is used for correction, from the projection information;

a correction coefficient modifying device for modifying a second correction coefficient, which said correction coefficient producing device calculates using projection information acquired from a second phantom larger than a first phantom, using a first correction coefficient which said correction coefficient producing device calculates using projection information acquired from said first phantom; and a correcting device for correcting projection information, which is acquired from a subject positioned in the scan field, using the first correction coefficient and the modified second correction coefficient.

2. An X-ray CT system according to claim 1, wherein said correction coefficient producing device comprises:

a producing device for producing one sinogram using first projection information sampled in relation to all the views from projection information acquired from a phantom;

a beam-hardening correction device for correcting the first projection information in terms of the beam-hardening effect so as to produce second projection information;

a first fitting device for fitting a first function to the second projection information so as to produce third projection information; and a second fitting device for fitting a second function to the third projection information values that are provided as functions having as independent variables the second projection information values sampled in relation to all the views and each of the channels of said X-ray detector.

3. An X-ray CT system according to claim 1, wherein:

said X-ray detector is formed with a plurality of detection modules each assigned a predetermined number of channels; and said correction coefficient modifying device separates a plurality of reflections of high-frequency components from correction coefficient data calculated using the second phantom so as to leave a plurality of dependencies on a plurality of detection characteristics of said detection modules, and synthesizes the correction coefficient data, from which the reflections of high-frequency components are separated, with a plurality of reflections of high-frequency components in correction coefficient data calculated using the first phantom.

4. An X-ray CT system according to claim 3, wherein said detection modules are manufactured as united bodies in units of a channel.

5. An X-ray CT system according to claim 1, wherein said first and second phantoms have circular sections, and the diameter of said second phantom is larger than the diameter of said first phantom.

6. An X-ray CT system according to claim 1, wherein said X-ray detector is formed using a combination of a scintillator and a photodiode.

7. An X-ray CT system according to claim 1, wherein said X-ray detector has an X-ray incidence surface curved like a cylindrical concave surface.

8. An X-ray CT system according to claim 1, wherein said X-ray detector has a plurality of X-ray detection elements set in an array in a direction in which X-rays spread in the form of a fan.

9. A beam-hardening post-processing method for X-ray CT systems according to which an X-ray detector having multiple channels is used to detect projection information, which is provided by an X-ray beam having passed through a scan field, as a plurality of views from a plurality of directions, and projection information detected on each channel is corrected in terms of a beam-hardenmnn effect, comprising:

an acquiring step of scanning a first phantom and a second phantom, which is larger than said first phantom, disposed between an X-ray tube and said X-ray detector, and acquiring projection information as a plurality of views from plural directions using said X-ray detector having multiple channels;

a producing step of producing first and second correction coefficients, which are used for correction, from projection information acquired from said first and second phantoms;

a modifying step of modifying the second correction coefficient using the first correction coefficient; and a correcting step of correcting projection information, which is acquired from a subject positioned in the scan field, using the first correction coefficient and the modified second correction coefficient.

10. A beam-hardening post-processing method for X-ray CT systems according to claim 9, wherein:

at said acquiring step, first projection information is sampled from projection information acquired from said first and second phantoms in relation to all the views in order to produce a plurality of sinograms;

at said producing step, the first projection information is corrected in terms of the beam-hardening effect in order to produce second projection information;

a first function is fitted to the second projection information in order to produce third projection information; and a second function is fitted to the third projection information values that are provided as functions having as independent variables the second projection information values sampled in relation to all the views and each of the channels of said X-ray detector in order to calculate the first and second correction coefficients.

11. A beam-hardening post-processing method for X-ray CT systems according to claim 9, wherein:

said X-ray detector is formed with a plurality of detection modules each assigned a predetermined number of channels; and at said modifying step, a plurality of reflections of high-frequency components are separated from correction coefficient data calculated using said second phantom in order to leave a plurality of dependencies on a plurality of detection characteristics of said detection modules, and the correction coefficient data from which the reflections of high-frequency components are separated is synthesized with a plurality of reflections of high-frequency components in correction coefficient data calculated using said first phantom.

12. A beam-hardening post-processing method for X-ray CT systems according to claim 11, wherein said detection modules are manufactured as united bodies in units of a channel.

13. A beam-hardening post-processing method for X-ray CT systems according to claim 9, wherein phantoms having circular sections are adopted as said first and second phantoms, and the diameter of said second phantom is larger than the diameter of said first phantom.

14. A beam-hardening post-processing method for X-ray CT systems according to claim 9, wherein said X-ray detector is formed using a combination of a scintillator and a photodiode.

15. A beam-hardening post-processing method for X-ray CT systems according to claim 9, wherein said X-ray detector has an X-ray incidence surface curved like a cylindrical concave surface.

16. A beam-hardening post-processing method for X-ray CT systems according to claim 9, wherein said X-ray detector has a plurality of X-ray detection elements set in array in a direction in which X-rays spread in the form of a fan.

* * * * *

UNITED STATES PATENT AND TRADEMARK OFFICE
CERTIFICATE OF CORRECTION

| | | |
|---|---|---|
| PATENT NO. | : 7,088,800 B2 | Page 1 of 1 |
| APPLICATION NO. | : 10/825526 | |
| DATED | : August 8, 2006 | |
| INVENTOR(S) | : Nukui et al. | |

It is certified that error appears in the above-identified patent and that said Letters Patent is hereby corrected as shown below:

In Claim 9, column 13, line 2, delete "beam-hardemnmn" and insert therefor -- beam-hardening --.

In Claim 16, column 14, beginning on line 33, between "in" and "array," insert -- an --.

Signed and Sealed this

Twenty-ninth Day of April, 2008

JON W. DUDAS
*Director of the United States Patent and Trademark Office*